(12) United States Patent
Tsuji et al.

(10) Patent No.: US 7,625,757 B2
(45) Date of Patent: Dec. 1, 2009

(54) REAGENT FOR IMMATURE LEUKOCYTE ANALYSIS AND REAGENT KIT

(75) Inventors: Tomohiro Tsuji, Kobe (JP); Ayumu Yoshida, Kobe (JP); Shinichiro Oguni, Kobe (JP)

(73) Assignee: Sysmex Corporation, Hyogo (JP)

( * ) Notice: Subject to any disclaimer, the term of this patent is extended or adjusted under 35 U.S.C. 154(b) by 176 days.

(21) Appl. No.: 11/650,962

(22) Filed: Jan. 9, 2007

(65) Prior Publication Data
US 2007/0178597 A1 Aug. 2, 2007

(30) Foreign Application Priority Data
Jan. 27, 2006 (JP) .............. 2006-019895

(51) Int. Cl.
*G01N 31/00* (2006.01)
*G01N 33/48* (2006.01)

(52) U.S. Cl. .............. 436/10; 436/8; 436/17; 436/63; 436/164; 436/166; 436/175; 435/2; 422/61; 252/408.1

(58) Field of Classification Search ........ 436/8, 436/10, 17, 63, 164, 166, 174, 175; 252/408.1; 435/2; 422/61
See application file for complete search history.

(56) References Cited

U.S. PATENT DOCUMENTS

| | | | |
|---|---|---|---|
| 5,094,854 A * | 3/1992 | Ogawa et al. | 424/423 |
| 5,389,549 A * | 2/1995 | Hamaguchi et al. | 436/10 |
| 5,413,938 A * | 5/1995 | Tsujino et al. | 436/63 |
| 5,958,776 A | 9/1999 | Sakata et al. | |
| 6,790,652 B1 | 9/2004 | Terry et al. | |
| 6,916,658 B2 * | 7/2005 | Li et al. | 436/10 |
| 7,413,905 B2 * | 8/2008 | Xu et al. | 436/10 |

FOREIGN PATENT DOCUMENTS

| | | |
|---|---|---|
| EP | 0 525 398 A2 | 2/1993 |
| EP | 0 743 519 A2 | 11/1996 |
| EP | 0 806 664 A2 | 11/1997 |
| EP | 0 844 481 A1 | 5/1998 |
| EP | 0 867 720 A1 | 9/1998 |
| EP | 1 542 008 A1 | 6/2005 |
| WO | WO 2006/086157 A1 | 8/2006 |

* cited by examiner

*Primary Examiner*—Maureen M Wallenhorst
(74) *Attorney, Agent, or Firm*—Sughrue Mion, PLLC

(57) ABSTRACT

A reagent for analyzing immature leukocyte capable of analyzing accurately immature leukocyte such as myeloblast and immature granulocyte, and mature leukocyte, which reagent has broader allowable range of sample processing conditions than conventional ones, and a reagent kit are provided. The present invention relates to a reagent for analyzing immature leukocyte containing a surfactant for giving damage to cell membrane of red blood cell and mature leukocyte in the sample, a solubilizing agent for causing contraction to damaged blood cell, sugar, a dye for staining nucleic acid.

18 Claims, 16 Drawing Sheets

REAGENT FOR IMMATURE LEUKOCYTE ANALYSIS AND REAGENT KIT

FIELD OF THE INVENTION

The present invention relates to a reagent and a reagent kit for classifying and counting leukocytes contained in a sample taken from a living body.

BACKGROUND

Blood cells are produced in the bone marrow, differentiated from immature cells, grown matured, and migrate to peripheral blood. In healthy adults, immature leukocyte does not appear in peripheral blood, however, immature leukocyte may appear in peripheral blood in patients with leukemia, metastatic bone marrow cancer, severe infectious disease. Therefore, it is extremely important to determine mature leukocytes and immature leukocytes in a biological sample for diagnosis of above-mentioned disorders.

As reagents for leukocyte determination, those disclosed in U.S. Pat. No. 5,958,776 are known. When a measurement sample in which the reagent and a biological sample are mixed is introduced into a flow cytometer and a light with specific wavelength is irradiated to obtain optical information, it is possible to classify mature leukocytes and immature leukocytes in the specimen based on the optical information and to count them, respectively. Further, it is possible to divide immature leukocytes into myeloblast and immature granulocyte and to count them, respectively. However, when a sample containing immature leukocytes was processed using this reagent, damage of immature leukocytes such as myeloblast was promoted in some cases, depending on processing conditions thereby resulting in deterioration of the classification accuracy. Therefore, in order to execute accurately classification or counting of immature leukocytes in the sample using the reagent, it was necessary to observe stringent control of processing conditions such as reaction temperature, reaction time or the like.

SUMMARY OF THE INVENTION

The scope of the present invention is defined solely by the appended claims, and is not affected to any degree by the statements within this summary.

The present invention provides a reagent for immature leukocyte analysis containing a surfactant that gives damage to cell membrane of red blood cell and mature leukocyte in a sample, a solubilizing agent that causes contraction to damaged blood cells, sugar, and a dye for staining nucleic acid.

Further, the present invention provides a reagent kit for immature leukocyte analysis containing a first reagent including a surfactant that gives damage to cell membrane of red blood cell and mature leukocyte, a solubilizing agent that causes contraction to damaged blood cells, and osmotic pressure regulator, which reagent having osmotic pressure from 150 to 600 mOsm/kg, and electric conductivity of less than 6 mS/cm; and a second reagent including a dye for staining nucleic acid.

Further, the present invention provides a reagent kit for immature leukocyte analysis containing a first reagent including a surfactant that gives damage to cell membrane of red blood cell and mature leukocyte, a solubilizing agent that causes contraction to damaged blood cells, and sugar; and a second reagent including a dye for staining nucleic acid.

According to the present invention, it is possible to analyze immature leukocytes and mature leukocytes with good accuracy, and a reagent and a reagent kit for immature leukocytes analysis with broader allowable range of processing conditions of the sample than conventional ones are provided.

DESCRIPTION OF REFERENCE NUMERALS

Figure 1:
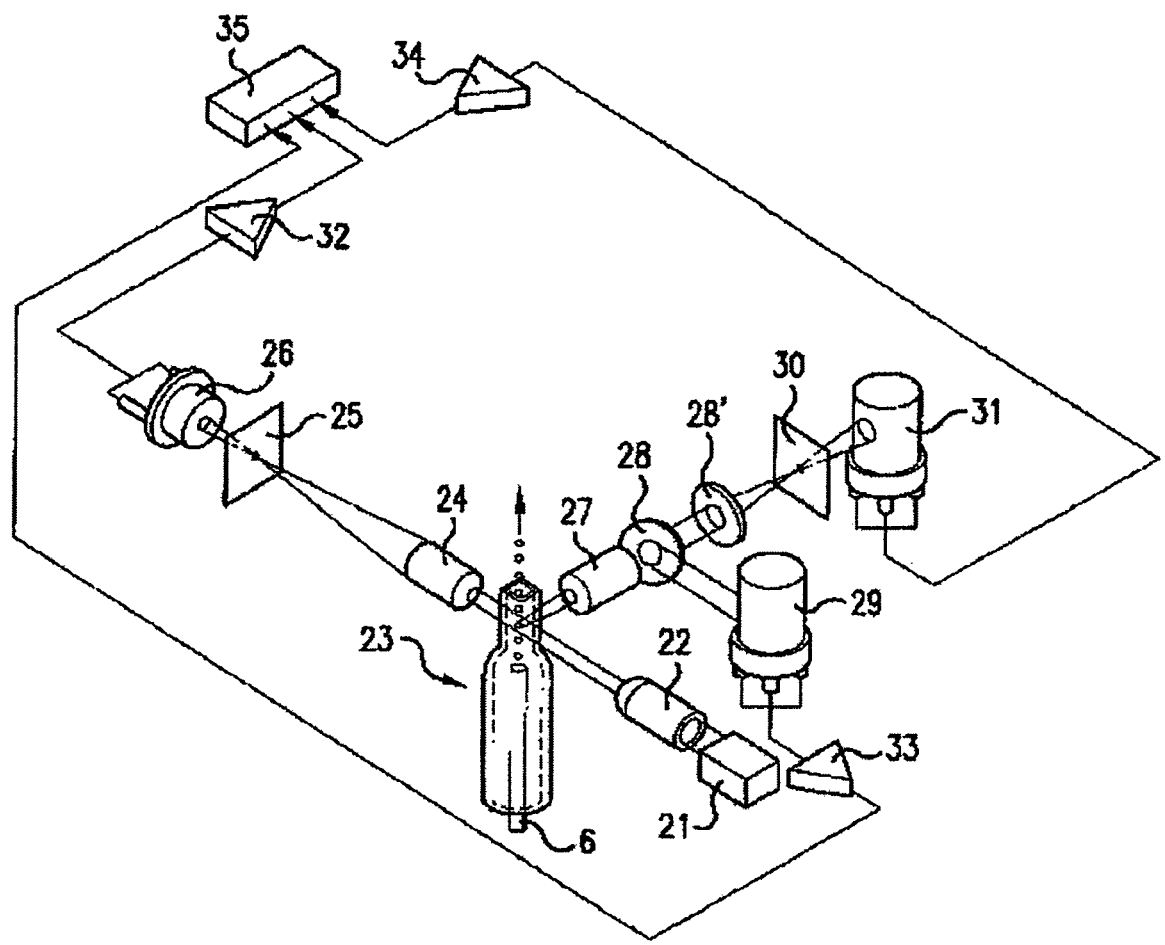
FIG. 1 shows a flow cytometer.

| | |
|---|---|
| 6: Nozzle | 21: Light source |
| 22: Collimated lens | 23: Flow cell |
| 24: Collecting lens | 25: Pinhole plate |
| 26: Forward-scattered light detector | |
| 27: Collecting lens | 28: Dichroic mirror |
| 29: Side-scattered light detector | |
| 30: Pinhole plate | |
| 31: Side-fluorescence detector | |
| 32: Amplifier | 33: Amplifier |
| 34: Amplifier | 35: Analyzer unit |

DETAILED DESCRIPTION OF THE EMBODIMENT

With the use of an immature leukocyte analysis reagent (hereafter referred simply to as the regent) according to the embodiment, it is possible to classify white blood cells contained in a sample into mature leukocytes and immature leukocytes and to count them, respectively. It is also possible to divide mature leukocytes into lymphocytes, monocytes and granulocytes and count them, respectively. Especially when the reagent is used, it is possible to further classify immature leukocytes into immature granulocytes and myeloblasts and to count them with good accuracy.

"Immature leukocyte" as used herein means immature white blood cell which is not present in the peripheral blood of healthy individuals, but is present in the bone marrow. For example, myeloblast, promyelocyte, medullocell, metamyelocyte or the like are mentioned. Promyelocyte, medullocell, metamyelocyte are sometimes referred to as the immature granulocyte. Myeloblast also includes hematopoietic precursor cell of white blood cell system such as bone marrow stem cell (CFU-GEMN), neutrophil, macrophage colony forming cell (CFU-GM), eosinophil colony forming cell (CFU-EOS) or the like.

For biological sample to be used for the measurement, there is no particular restriction as long as the sample includes white blood cell; and blood, urine, bone marrow aspirate, and sample taken by apheresis may be exemplified.

The reagent according to the embodiment includes surfactant that gives damage to cell membrane of red blood cell and mature leukocyte, solubilizing agent that causes damaged blood cell to constrict and nucleic acid staining dye. When the biological sample and reagent are mixed, cell membrane of blood cell contained in the sample is damaged by the action of surfactant. Although this surfactant gives damage to cell membrane of red blood cell and mature leukocyte, it does not give substantial damage to cell membrane of immature leukocyte. Damaged blood cell of red blood cell, mature leukocyte or the like cause constriction by the action of solubilizing agent. Since cell membrane of immature leukocyte is being hardly damaged, constriction of cells by the solubilizing agent is more unlikely to happen than red blood cell and mature leukocyte. Although nuclei of damaged blood cell are stained by the action of dye, immature leukocyte is hardly stained.

For the surfactant, for example, polyoxyethylene-type nonionic surfactant may be used. Specifically, those having the following chemical formula may be used:

$R_1—R_2—(CH_2CH_2O)_n—H$ (In the formula, $R_1$ denotes alkyl group, alkenyl group or alkynyl group having from 10 to 25 carbon numbers, $R_2$ denotes —O— or

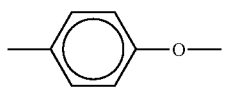

or —COO—, where n is from 10 to 40.)

It is particularly preferable to use polyoxyethylene (16) oleyl ether, polyoxyethylene (20) lauryl ether, polyoxyethylene (15) oleyl ether or the like.

Preferable concentration of the surfactant to be contained by the reagent is depending on types of the surfactant. When polyoxyethylene (16) oleyl ether is used, for example, from 1000 to 50000 ppm is preferable, from 10000 to 35000 ppm is more preferable. The surfactant may be used alone or more than two types of surfactants may be used together.

For the solubilizing agent, for example, sarcosine derivative or salt thereof, cholic acid derivative, methylglucamide or the like may be used.

Sarcosine derivative has the following chemical formula:

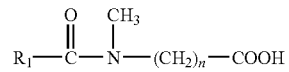

(In the formula, $R_1$ denotes alkyl group having from C10 to 22, and n is from 1 to 5.)

Cholic acid derivative has the following chemical formula:

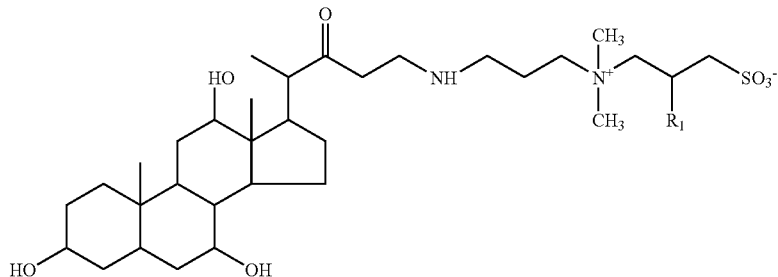

(In the formula, $R_1$ is hydrogen atom or hydroxyl group.)

Methylglucamide has the following chemical formula:

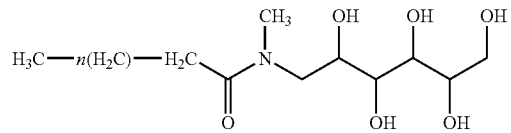

(In the formula, n is from 5 to 7.)

When sarcosine derivative or salt thereof is used, its concentration in the reagent is preferably from 200 to 3000 ppm. When cholic acid derivative is used, its concentration is preferably from 100 to 1000 ppm. When methylglucamide is used, its concentration is preferably from 1000 to 8000 ppm.

As for concrete example of sarcosine derivative or salt thereof, N-lauroyl sarcosine sodium, lauroyl methyl β-alanine sodium, lauroyl sarcosine or the like are mentioned. As for concrete example of cholic acid derivative or salt thereof, CHAPS (3-[(3-cholamidopropyl)dimethylammonio]-1-propane sulfonate), CHAPSO ([3-cholamidopropyl]dimethylammonio)-2-hydroxy-1-propane sulfonate) or the like are mentioned. As for concrete example of methylglucamide, MEGA8 (octanoyl-N-methylglucamide), MEGA9 (nonanoyl-N-methylglucamide), MEGA10 (decanoyl-N-methylglucamide) or the like are mentioned.

In addition to the above, as the solubilizing agent, it is possible to use n-octyl β-glycoside, sucrose monocaprate, N-formylmethylleucyl alanine. When these are used, their concentration in the reagent is preferably from 10 to 50000 ppm. The solubilizing agent may be used alone or more than two types of solubilizing agents may be used together.

As for the dye, there is no particular restriction as long as it specifically stains nucleic acid, while fluorescent dye is preferred. By using such dyes, red blood cell without nucleus is hardly stained, while white blood cell with nucleus is strongly stained. Based on the difference of staining strength as mentioned, it is possible to discriminate red blood cell and white blood cell. Further, mature leukocyte having cell membrane heavily damaged as to allow transmission of dyes is strongly stained, while immature leukocyte is hardly stained. Based on the difference of staining strength as mentioned, it is possible to discriminate, of white blood cells, mature leukocyte and immature leukocyte. The type of dye is selected appropriately depending on the light being irradiated. For example, when helium-neon laser or red semiconductor laser is used as the light source, it is preferable to use dyes having the following chemical formula:

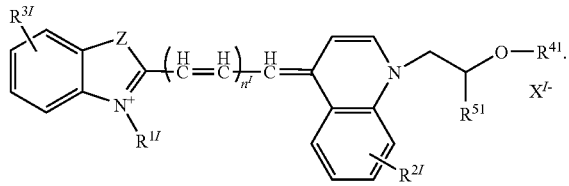

(wherein $R^{1I}$ is hydrogen atom or a lower alkyl group; $R^{2I}$ and $R^{3I}$ are independently hydrogen atom, a lower alkyl group or a lower alkoxy groups; $R^{4I}$ is hydrogen atom, an acyl group or a lower alkyl group; $R^{5I}$ is hydrogen atom or an optionally substituted lower alkyl group; Z is sulfur atom, oxygen atom or carbon atom substituted with a lower alkyl group; n is 1 or 2; and $X^{I-}$ is an anion.)

In the formula, lower alkyl group in $R^{1I}$ is straight chain or branched chain alkyl group having from 1 to 6 carbon numbers.

For example, methyl group, ethyl group, propyl group, butyl group, isobutyl group, sec-butyl group, ter-butyl group, pentyl group, hexyl group or the like are mentioned, and of them, methyl group and ethyl group are preferable.

Lower alkyl groups in $R^{2I}$ and $R^{3I}$ are the same as above, and as for lower alkoxy group, alkoxy having from 1 to 6 carbon numbers is meant. For example, methoxy group, ethoxyl group, propoxy group or the like are mentioned, while of them, methoxy group and ethoxyl group are preferable. Meanwhile, $R^{2I}$ and $R^{3I}$ are preferably hydrogen atom.

As for acyl group in $R^{4I}$, acyl group derived from aliphatic carboxylic acid is preferable. Specifically, acetyl group, propionyl group or the like are mentioned, and of them, acetyl group is preferable. Further, lower alkyl group is similar to the above.

Lower alkyl group in $R^{5I}$ is similar to the above, and lower alkyl group that may be substituted denotes lower alkyl group that may be substituted with from 1 to 3 hydroxy groups, halogen atom (fluorine, chlorine, bromine or iodine) or the like. Of them, methyl group and ethyl group substituted with one hydroxy group is preferable.

Lower alkyl group in Z is similar to the above, and as for Z, sulfur atom is preferable.

As for anion in $X^{I-}$, halogen ion (fluorine, chlorine, bromine or iodine ion), boron halogenide ion (BF4-, BCl4-, BBr4- or the like), phosphide compound ion, halogen oxyacid ion, fluorosulfuric acid ion, methylsulfuric acid ion, tetraphenyl borate compound ion having alkyl group having aromatic ring halogen or halogen as the substitution group, or the like are mentioned.

Of them, bromine ion or BF4- is preferable.

As for concrete example of dyes in above-mentioned (I), the following dyes are preferred:

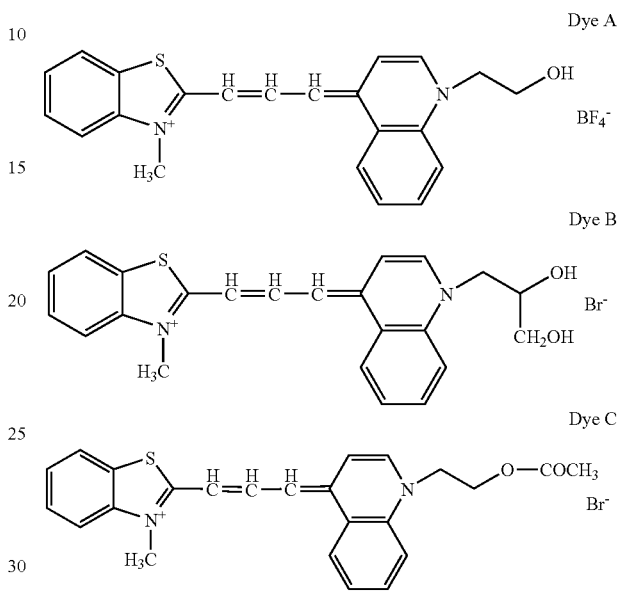

In addition to dyes mentioned above, propidiumiodide, ethidiumbromide, ethidium-acridineheterodimmer, ethidiumdiazide, ethidiumhomodimer-1, ethidiumhomodimer-2, ethidiummonoazide, TOTO-1, TO-PRO-1, TOTO-3, TO-PRO-3, iodine green, NK-3975 (Hayashibara Biology Laboratory), NK-1570 (Hayashibara Biology Laboratory), NK-1049 (Hayashibara Biology Laboratory) or the like are used preferably.

The concentration of above-mentioned dyes in the reagent is preferably from 0.01 to 500 ppm, more preferably from 0.1 to 200 ppm. The dye may be used alone or more than two types of dyes may be used together.

The osmotic pressure of the reagent is preferably adjusted to from 150 to 600 mOsm/kg. In order to adjust the osmotic pressure of the reagent to a desired range, the reagent contains sugar. Even if reaction time is lengthened or reaction temperature is increased by adjustment of the osmotic pressure of the reagent using sugar, myeloblast is hardly damaged, and it is possible to classify myeloblast and mature leukocyte and to count them accurately.

As a substance for adjusting the osmotic pressure (osmotic pressure regulator), sodium chloride may be also contained in the reagent. However, when the reagent contains a large amount of sodium chloride, after mixing of the reagent with the sample, damage of myeloblast is accelerated as the reaction time is elapsed or the reaction temperature is increased, and nuclei of myeloblast are stained by the dye. When myeloblast is stained, fluorescence intensity being detected becomes equal to that of mature leukocyte, and accuracy of classification of mature leukocyte and myeloblast is reduced. From the above, for the sake of elimination of bad effects upon measurements, concentration of sodium chloride in the reagent is preferably from 0.01 to 3 g/L, and 0 g/L (not contained) is more preferable.

Although the type of sugar to be contained in the reagent is not limited in particular, monosaccharide, polysaccharide, sugar alcohol or the like may be used. For monosaccharide, glucose, fructose or the like are exemplified; for polysaccharide, arabionose or the like are exemplified; for sugar alcohol, xylitol, sorbitol, mannitol, ribitol are exemplified. Sugar concentration in the reagent is preferably from 10 to 75 g/L, more preferably from 20 to 50 g/L. Of these sugars, one type may be used or more than two types may be used together.

In order to adjust pH of the reagent, it is preferable to add buffering agent to the reagent. For the buffering agent, Good's buffer such as HEPES, phosphoric acid buffering agent, or the like may be used, and pH osmotic pressure regulator such as sodium hydroxide may be used. It is preferable that pH of the reagent is adjusted to from 5.0 to 9.0.

Although each of above-mentioned components may be accommodated in the same container, it is preferable to accommodate them in more than two containers to form a reagent kit. The reagent kit includes a first reagent containing a surfactant to give damage to cell membrane of red blood cell and mature leukocyte, a solubilizing agent to cause constriction to damaged blood cells, sugar and a second reagent containing dyes. In this case, in order to improve the preservation stability of dyes, dyes in the second reagent are preferably being dissolved in the organic solvent.

Further, a reagent kit according to another embodiment of the present invention includes a first reagent containing a surfactant to give damage to cell membrane of red blood cell and mature leukocyte, a solubilizing agent to cause constriction to damaged blood cells, osmotic pressure regulator; and a second reagent containing nucleic acid staining dye.

The osmotic pressure regulator is added to allow adjustment of osmotic pressure and electric conductivity of the first reagent to a desired level. By using this osmotic pressure regulator, the osmotic pressure of the first reagent is adjusted to from 150 to 600 mOsm/kg. The electric conductivity of the first reagent is adjusted to less than 6 mS/cm, preferably from 0.01 to 3 mS/cm, more preferably from 0.1 to 2 ms/cm.

For osmotic pressure regulator, sugar, amino acid or the like may be used. For amino acid, valine, proline, glycine, alanine or the like may be used, while it is preferable to use either of glycine or alanine, or both. For concentration of amino acid, from 1 to 50 g/L is preferable, and from 10 to 30 g/L is more preferable. When sodium chloride is further added to the reagent as the osmotic pressure regulator, its concentration in the reagent is preferably from 0.01 to 3 g/L, and 0 g/L is more preferable, so that, as mentioned previously, measurements of myeloblast may not be affected.

By mixing a reagent containing each of above-mentioned components with a biological sample to prepare a measurement sample, and by using a flow cytometer, immature leukocyte can now be analyzed.

Mixing ratio of the biological sample and reagent (mixed reagent of all reagents for reagent kit) is preferably from 1:10 to 1:1000. Reaction of blood cell in the biological sample with the reagent is preferably carried out for from 3 to 15 sec at from 20 to 40° C. When the reaction temperature is high, reaction time may be shortened, and when reaction temperature is low, reaction time may be lengthened.

When the flow cytometer is used for measurements of a sample, a light is irradiated to blood cells in the measurement sample flowing through the flow cell to acquire optical information such as scattering light and fluorescence or the like, and type of blood cell is identified based on this information.

Specifically, a flow cytometer as shown in FIG. 1 may be used. As one example of the present embodiment, measurement of myeloblast will be explained hereafter in detail referring to FIG. 1.

A measurement sample discharged from a nozzle 6 flows through an orifice part of a flow cell 23. On this occasion, blood cells in the sample pass through the orifice part in line. A light emitted from a light source 21 is irradiated via a collimated lens 22 to blood cells flowing through the flow cell 23. By irradiating a light to blood cells, side-scattered light, side-fluorescence and forward-scattered light are generated. Side-scattered light is incident to a side-scattered light detector (photomultiplier tube) 29 via a collecting lens 27 and a dichroic mirror 28. Side-fluorescence is incident to a side-fluorescence detector (photomultiplier tube) 31 via the collecting lens 27, the dichroic mirror 28, a filter 29 and a pinhole plate 30. Forward-scattered light is incident to a forward-scattered light detector (photodiode) 26 via a collecting lens 24 and a pinhole plate 25.

Forward-scattered light signal being output from the forward-scattered light detector 26, side-scattered light signal output from the side-scattered light detector 29, and side-fluorescence signal output from the side-fluorescence detector 31 are amplified respectively by an amplifier 32, an amplifier 33 and an amplifier 34, and enter into an analyzer unit 35.

The analyzer unit 35 calculates forward-scattered light intensity, side-scattered light intensity and fluorescence intensity from the forward-scattered light signal, side-scattered light signal and side-fluorescence signal received. The analyzer unit 35 generates a first two-dimensional distribution chart based on two axes of forward-scattered light intensity and fluorescence intensity and identifies on this two-dimensional chart a region where total leukocyte in the sample appear (total leukocyte region). Further, it generates a second two-dimensional distribution chart based on two axes of side-scattered light intensity and fluorescence intensity for cells appearing on the total leukocyte region. On this two-dimensional distribution chart, a region where mature leukocytes appear (mature leukocyte region), a region where lymphocytes appear (lymphocyte region), a region where monocytes appear (monocyte region), and a region where granulocytes appear (granulocyte region) are set. Further, a region where myeloblasts appear (myeloblast region) and a region where immature granulocytes appear (immature granulocyte region) are identified. The number of cells appearing on the myeloblast region is counted as the number of myeloblasts contained in the sample, and the number of cells appearing on the immature granulocyte region is counted as the number of immature granulocyte contained in the sample. In the meantime, myeloblast is small in cell size and is of single nucleus, and therefore, forward-scattered light intensity is strong and side-scattered light intensity is weak. In addition, as mentioned previously, myeloblast is hardly stained, and therefore, its fluorescence intensity is weak. Immature granulocyte is large in cell size and its nucleus is segmented, and therefore, its forward-scattered light intensity and side-scattered light intensity are weak. Further, since it is hardly stained as mentioned before, its fluorescence intensity is weak.

EXAMPLE

Example 1

A first reagent A and a second reagent with the following compositions were prepared:

<First Reagent A>

Polyoxyethylene (16) oleyl ether (Nikko Chemicals) 20000 ppm, N-lauroyl sarcosine sodium 500 ppm, arabinose 39.6 g/LHEPES, 1 L of 10 mM purified water were mixed, and NaOH was added to adjust pH to 7.0. Osmotic pressure of the first reagent A was 280 mOsm/kg and electric conductivity was 0.59 mS/cm.

<Second Reagent>

Dye A 20 ppm

Ethylene glycol 1 L

980 μL of the first reagent, 20 μL of the second reagent, 20 μL of blood sample A containing myeloblast were mixed, caused to react for seven sec at 33° C., and then side-scattered light intensity and forward-scattered light intensity were measured by the flow cytometer shown in FIG. 1. A red semiconductor laser was used as the light source.

Figure 2:
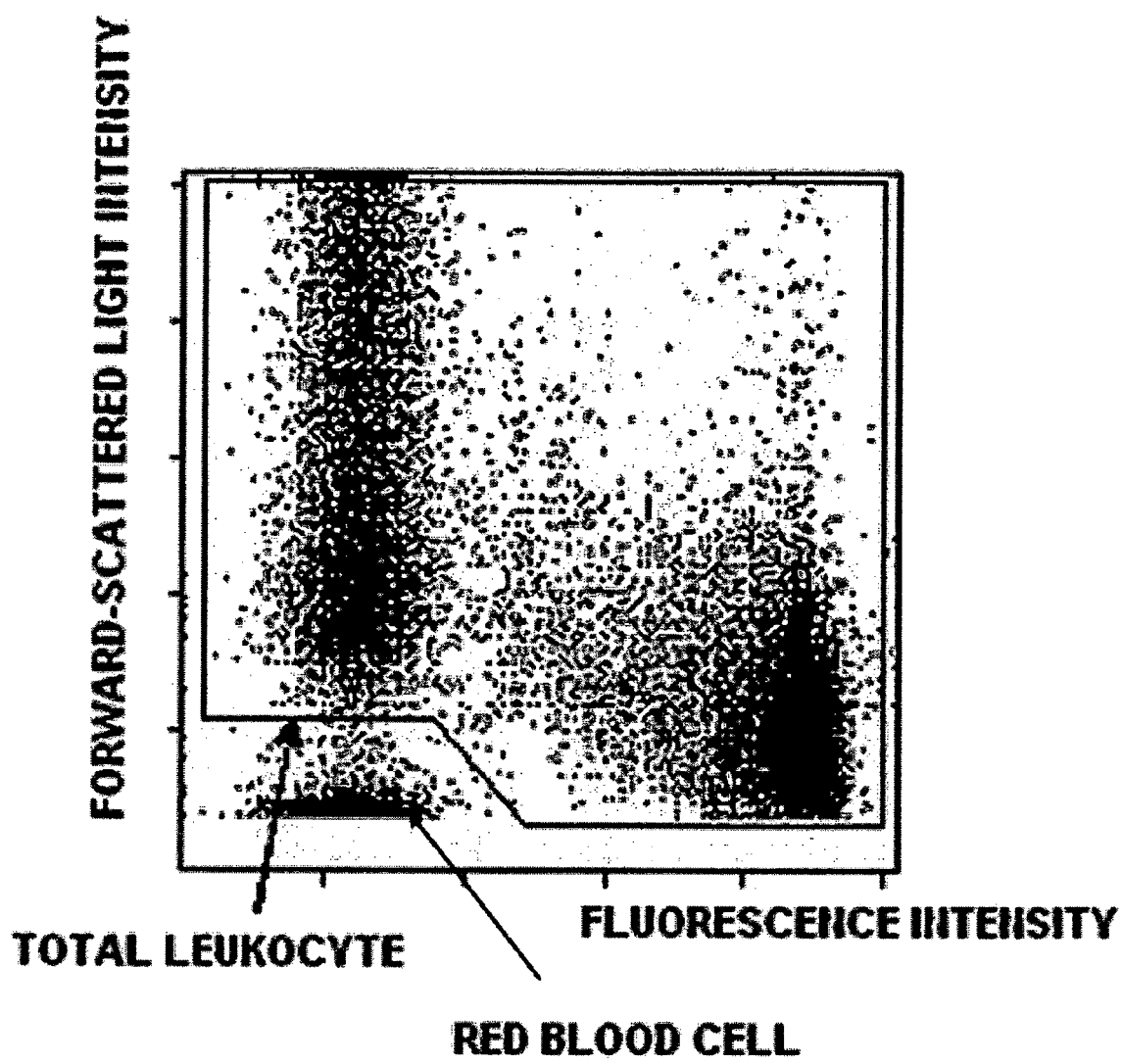
FIG. 2 is a first two-dimensional distribution chart in Example 1.

A first two-dimensional distribution chart based on two axes of side-scattered light intensity and fluorescent intensity obtained was prepared and total leukocyte region was identified. This is shown in FIG. 2. The number of cells appeared in the total leukocyte region was counted as the total leukocyte count.

Figure 3:
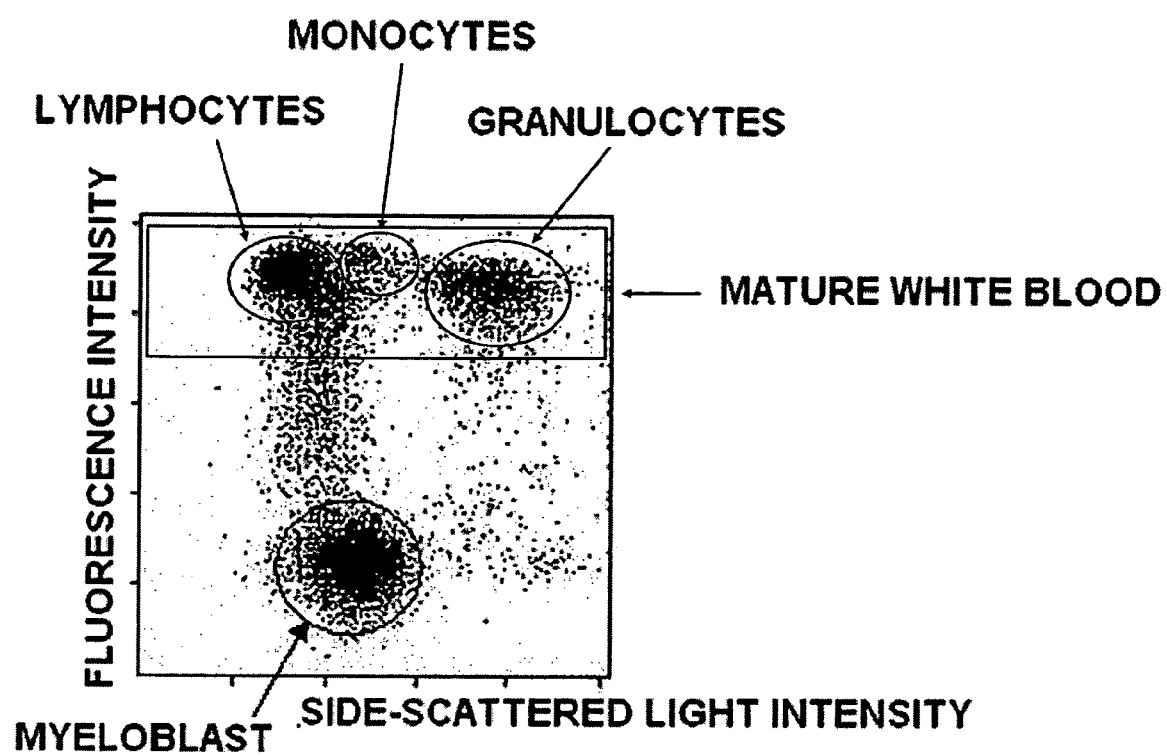
FIG. 3 is a second two-dimensional distribution chart in Example 1.

For cells appearing on the total leukocyte region in the first two-dimensional distribution chart, a second two-dimensional distribution chart based on two axes of side-scattered light intensity and fluorescence intensity was prepared, and a region where side-scattered light intensity was low and fluorescence intensity was low was identified as the myeloblast region. This is shown in FIG. 3. The number of cells appearing on the myeloblast region was counted as the number of myeloblasts.

In this example, ratio of myeloblast to total leukocyte count (Myeloblast ratio=Number of myeloblast/Total leukocyte count×100) was calculated. Myeloblast ratio was 45.8%.

Example 2

Figure 4:
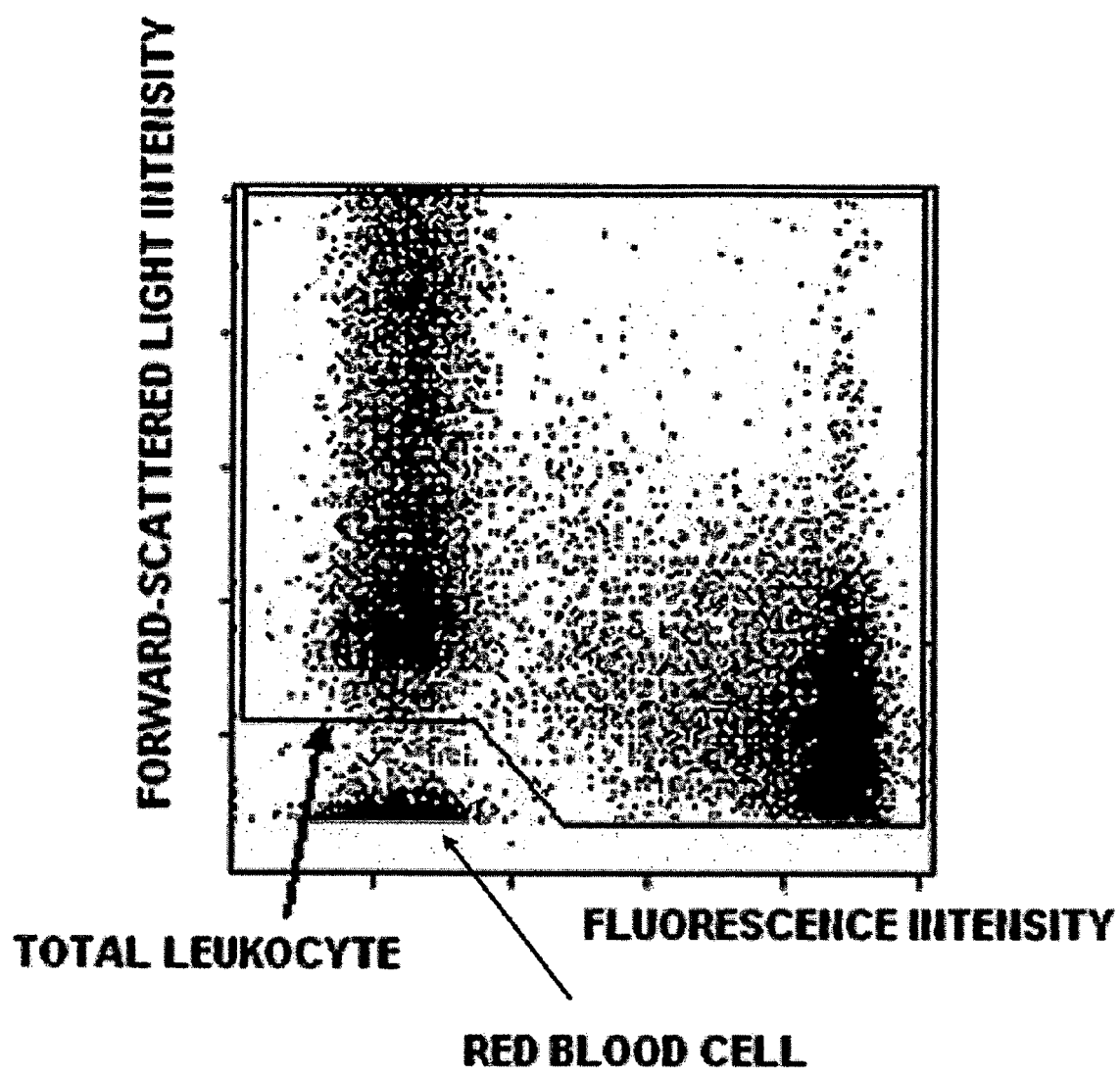
FIG. 4 is a first two-dimensional distribution chart in Example 2.
Figure 5:
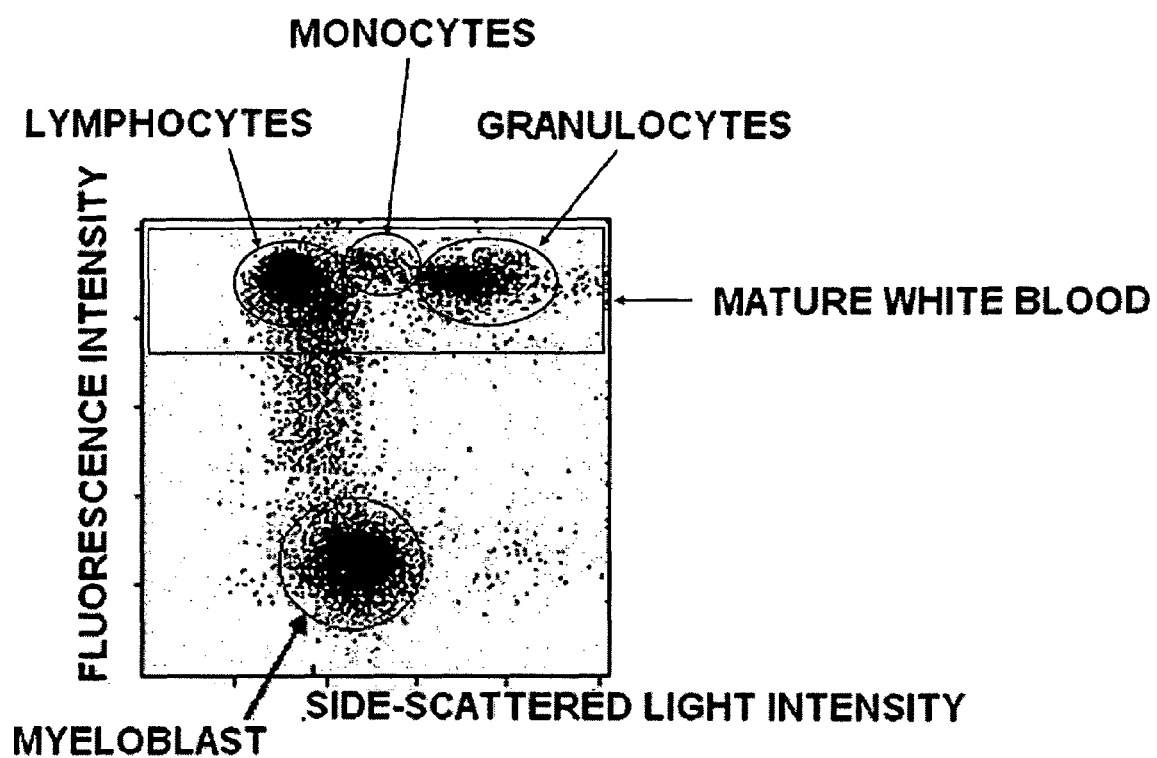
FIG. 5 is a second two-dimensional distribution chart in Example 2.

Myeloblast ratio was calculated similarly as Example 1 except that a reagent and blood sample A were reacted at 35° C. Myeloblast ratio was 42.6%. The first two-dimensional distribution chart prepared in Example 2 is shown in FIG. 4 and the second two-dimensional distribution chart is shown in FIG. 5.

Comparison Example 1

Myeloblast ratio was calculated similarly as Example 1 except that 1 mL of reagent containing polyoxyethylene (16) oleyl ether 24.0 g/L, N-lauroyl sarcosine sodium 1.5 g/L, DL-methionine 20.0 g/L, HEPES 12.0 g/L, 1N—NaOH 0.3 g/L, NaCl 4.0 g/L and dye A 3.0 mg/L, and 33 μL of blood sample B were mixed and reacted. Myeloblast ratio was 25.1%.

Figure 6:
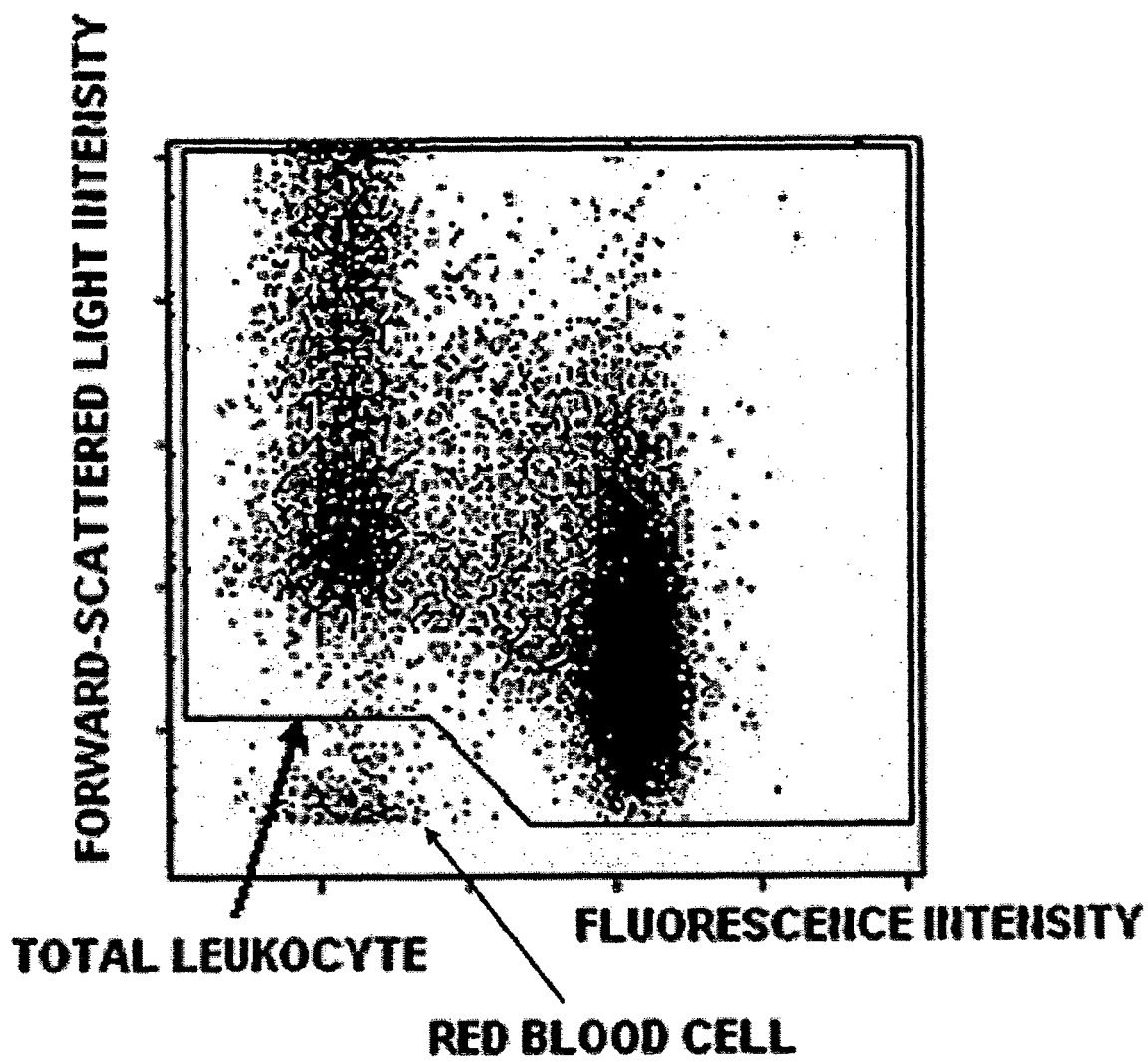
FIG. 6 is a first two-dimensional distribution chart in comparison example 1.
Figure 7:
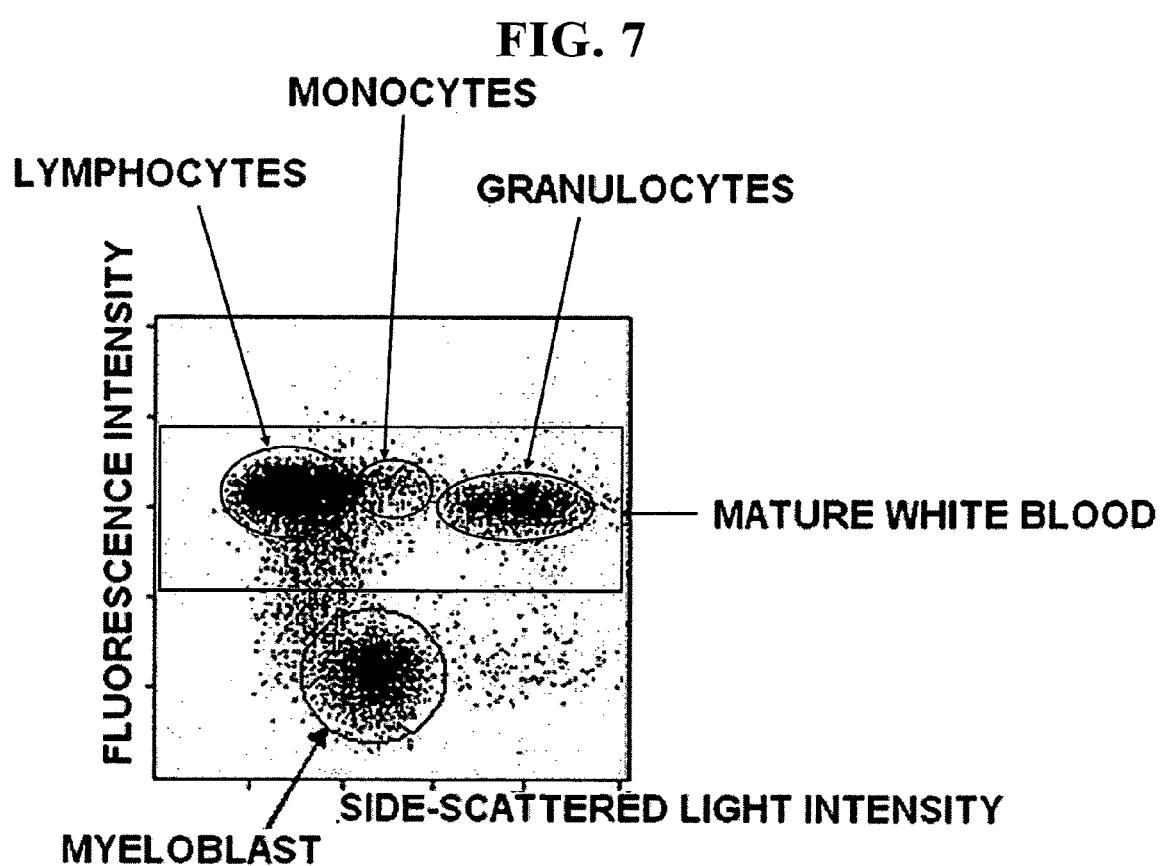
FIG. 7 is a second two-dimensional distribution chart in comparison example 1.

The first two-dimensional distribution chart prepared in Comparison Example 1 is shown in FIG. 6 and the second two-dimensional distribution chart is show in FIG. 7. Osmotic pressure of this reagent was 350 mOsm/kg and electric conductivity was 7.4 mS/cm.

Comparison Example 2

Figure 8:
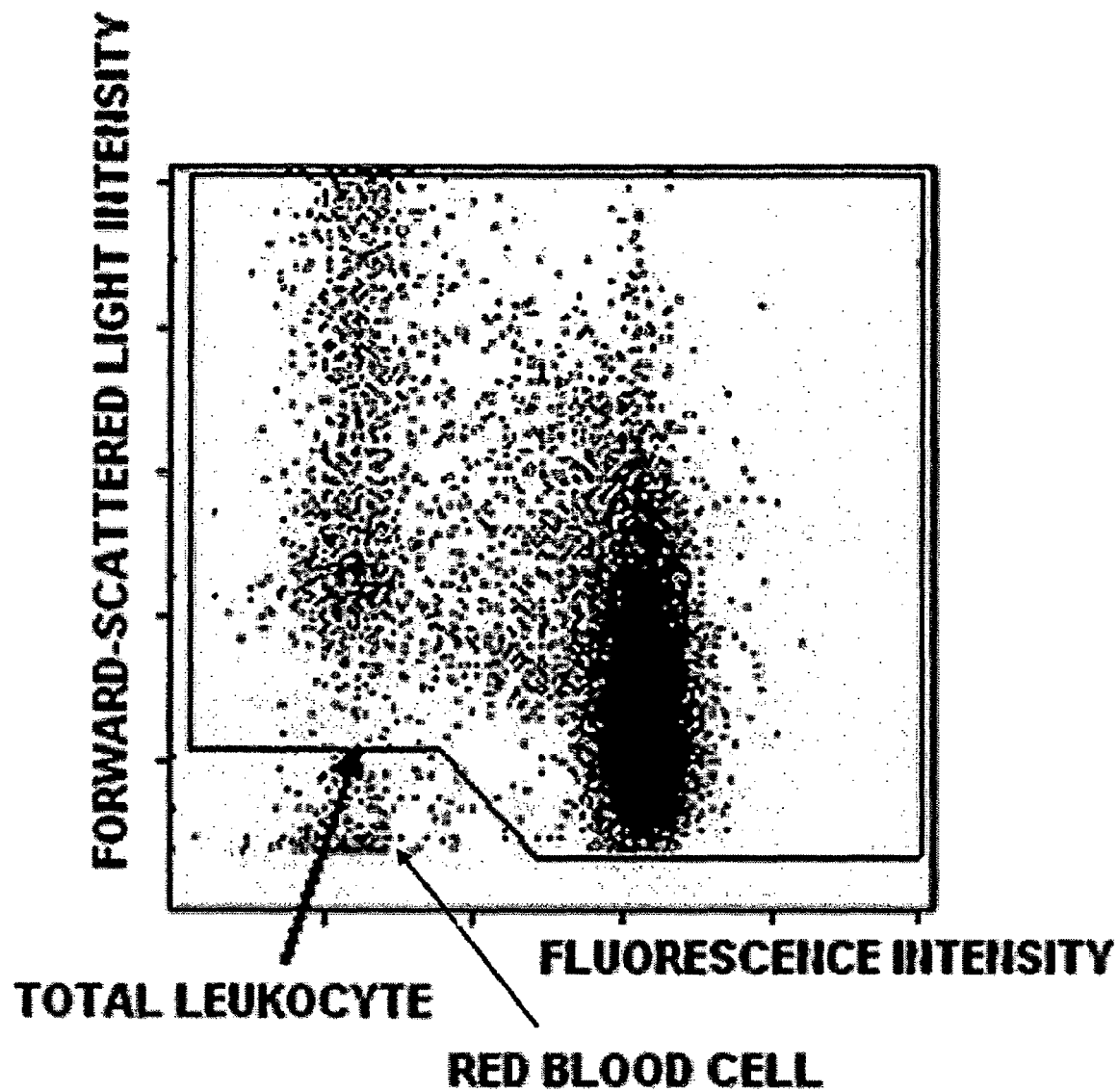
FIG. 8 is a first two-dimensional distribution chart in comparison example 2.
Figure 9:
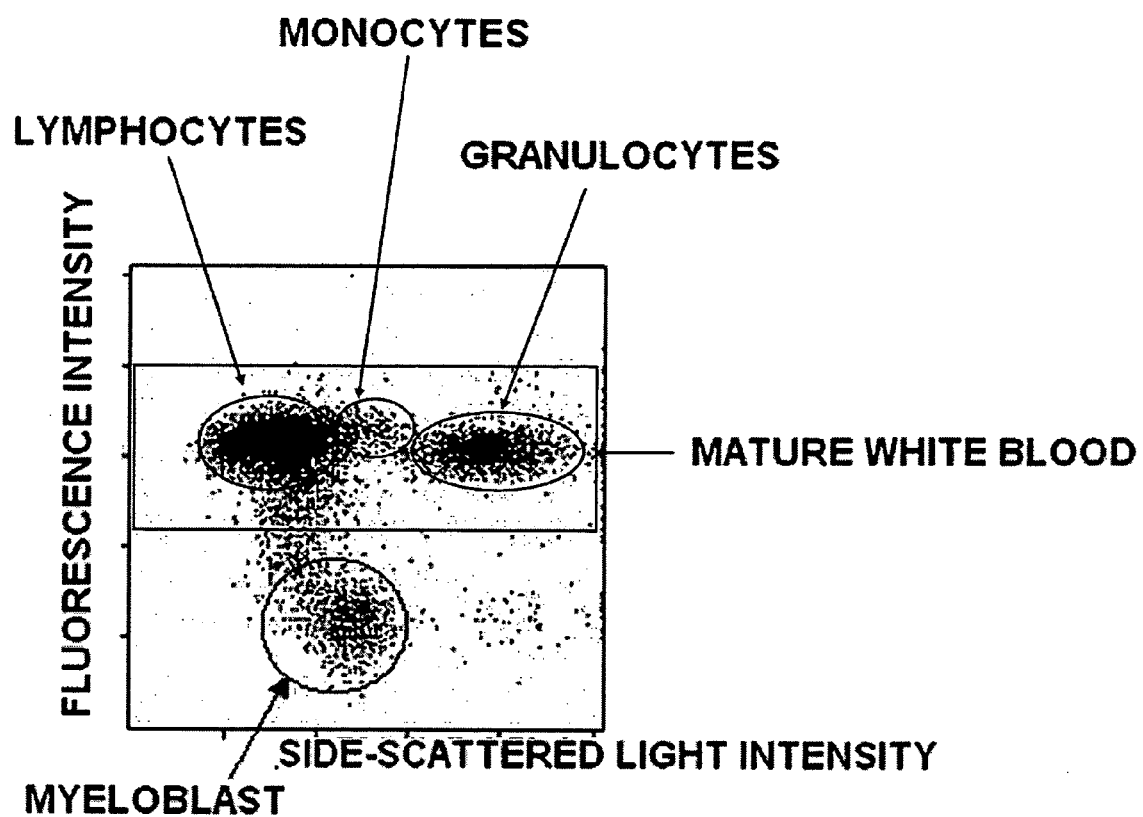
FIG. 9 is a second two-dimensional distribution chart in comparison example 2.

Myeloblast ratio was calculated similarly as Comparison Example 1 except that a reagent and blood sample B were reacted at 35° C. Myeloblast ratio was 7.2%. Meanwhile, the first two-dimensional distribution chart prepared in Comparison Example 2 is shown in FIG. 8 and the second two-dimensional distribution chart is shown in FIG. 9.

From Comparison Examples 1 and 2, compared to myeloblast ratio for reaction at 33° C. (Comparison Example 1), myeloblast ratio for reaction at 35° C. (Comparison Example 2) exhibited very low level even though the same blood sample was used. This is attributable to that when reacted at 35° C., myeloblast which should appear in the myeloblast region appeared outside the region. In other words, it is considered that when the reagents prepared in Comparison Examples 1 and 2 are used, myeloblast is unable to exist in stable manner as the reaction temperature becomes higher, and myeloblast is damaged during the reaction of seven sec.

However, from Examples 1 and 2, myeloblast ratio (Example 1) where reaction is caused at 33° C. is close to myeloblast ratio (Example 2) where reaction is caused at 35° C. This suggests that even the reagent prepared in the example and myeloblast are reacted at a high temperature, myeloblast is not damaged substantially and accurate counting is possible. Use of the reagent prepared in the example improved stability of myeloblast against temperature and it became hardly damaged. From above-mentioned observations, it has been confirmed that myeloblast in the sample can be measured accurately with the use of reagent prepared in the example.

Example 3

A first reagent B was prepared similarly as the first reagent A except that xylitol 39.56 g/L in lieu of arabinose, polyoxyethylene (16) oleyl ether 25000 ppm in lieu of 20000 ppm, N-lauroyl sarcosine sodium 750 ppm in lieu of 500 ppm were caused to be contained. Osmotic pressure of the first reagent B was 280 mOsm/kg and electric conductivity was 0.59 mS/cm.

Myeloblast ratio was calculated similarly as Example 1 except that first reagent B was used in lieu of first reagent A, and blood sample C was used in lieu of blood sample A. Further, myeloblast ratio was calculated similarly as Example 1 except that first reagent B was used in lieu of first reagent A, blood sample C was used in lieu of blood sample A, and the reagent was reacted with blood sample C for 12 sec in lieu of 7 sec.

Example 4

A first reagent C was prepared similarly as the first reagent B except that arabinose 39.52 g/L in lieu of xylitol was caused to be contained. Osmotic pressure of the first reagent C was 280 mOsm/kg and electric conductivity was 0.62 mS/cm.

Myeloblast ratio was calculated similarly as Example 3 except that first reagent C was used in lieu of first reagent B.

Example 5

A first reagent D was prepared similarly as the first reagent B except that alanine 23.16 g/L in lieu of xylitol was caused to be contained. Osmotic pressure of the first reagent D was 280 mOsm/kg and electric conductivity was 0.61 mS/cm.

Myeloblast ratio was calculated similarly as Example 3 except that first reagent D was used in lieu of first reagent B.

Example 6

A first reagent E was prepared similarly as the first reagent B except that glycine 19.52 g/L in lieu of xylitol was caused to be contained. Osmotic pressure of the first reagent E was 280 mOsm/kg and electric conductivity was 0.63 mS/cm.

Myeloblast ratio was calculated similarly as Example 3 except that first reagent E was used in lieu of first reagent B.

Comparison Example 3

Myeloblast ratio was calculated similarly as Example 1 except that blood sample C was used in lieu of blood sample A. Further, myeloblast ratio was calculated similarly as Example 1 except that blood sample D was used in lieu of blood sample A, and the reagent was reacted with blood sample C for 12 sec in lieu of 7 sec.

Figure 10:
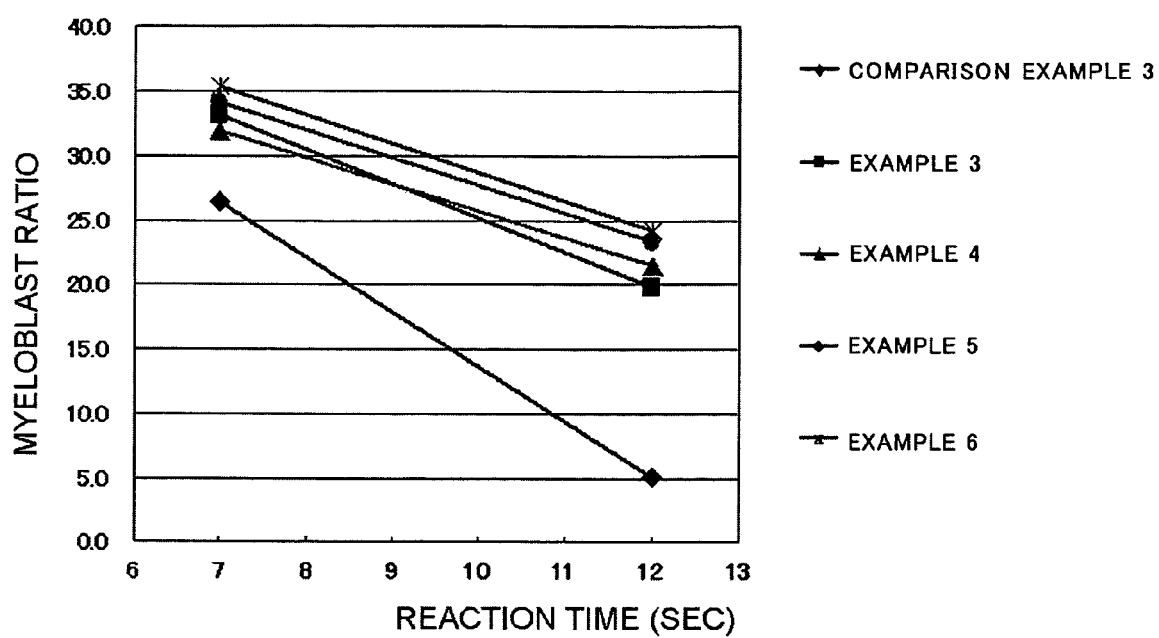
FIG. 10 is a graph showing results of examples 3 through 6 and comparison example 3.

Results of Examples 3 through 6 and Comparison Example 3 are shown in FIG. 10. FIG. 10 is a graph showing how much is reduced myeloblast ratio when the sample and reagent are reacted for 12 sec compared to myeloblast ratio when reacted for seven sec.

It is understood from FIG. 10 that when the reagent of Comparison Example 3 is used and caused to react with the sample for 12 sec, ratio of myeloblast is lowered more than 20% compared to the case of reaction for seven sec. This is considered to be attributable to that the longer the reaction time, the more the myeloblast was damaged by effects of the reagent.

When the reagent prepared in any of Examples 3 through 6 is used, reduction in myeloblast ratio could be suppressed to approximately 10% compared to the case where the reagent of Comparison Example 3 was used. Namely, by using the reagent of Examples 3 through 6, stability of myeloblast was improved and it became hardly damaged in the measurement sample. From above-mentioned observations, it has been confirmed that by using the reagent of Examples 3 through 6, myeloblast became hardly damaged and myeloblast could be measured accurately.

Example 7

A first reagent F containing the following compositions was prepared:

| | |
|---|---|
| Polyoxyethylene (16) oleyl ether | 25000 ppm |
| N-lauroyl sarcosine sodium | 750 ppm |
| Xylitol | 37.0 g/L |
| HEPES | 10 mM |
| Purified water | 1 L |

Above materials were mixed and NaOH was added to adjust pH to 7.0. Osmotic pressure of the first reagent F was 280 mOsm/kg and electric conductivity was 0.64 mS/cm. Further, for a second reagent, the same reagent as adjusted in Example 1 was used.

Figure 11:
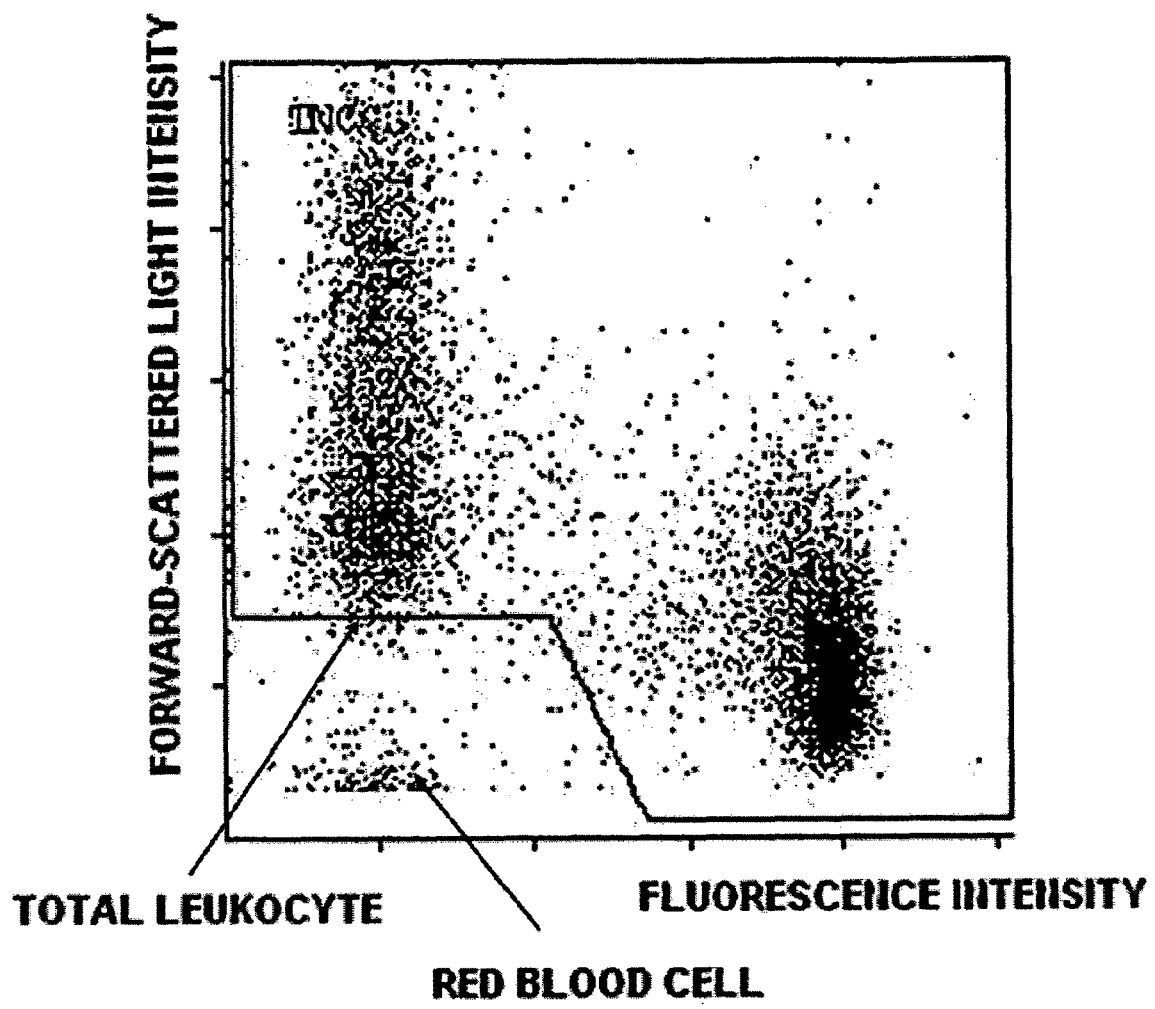
FIG. 11 is a first two-dimensional distribution chart in example 7.
Figure 12:
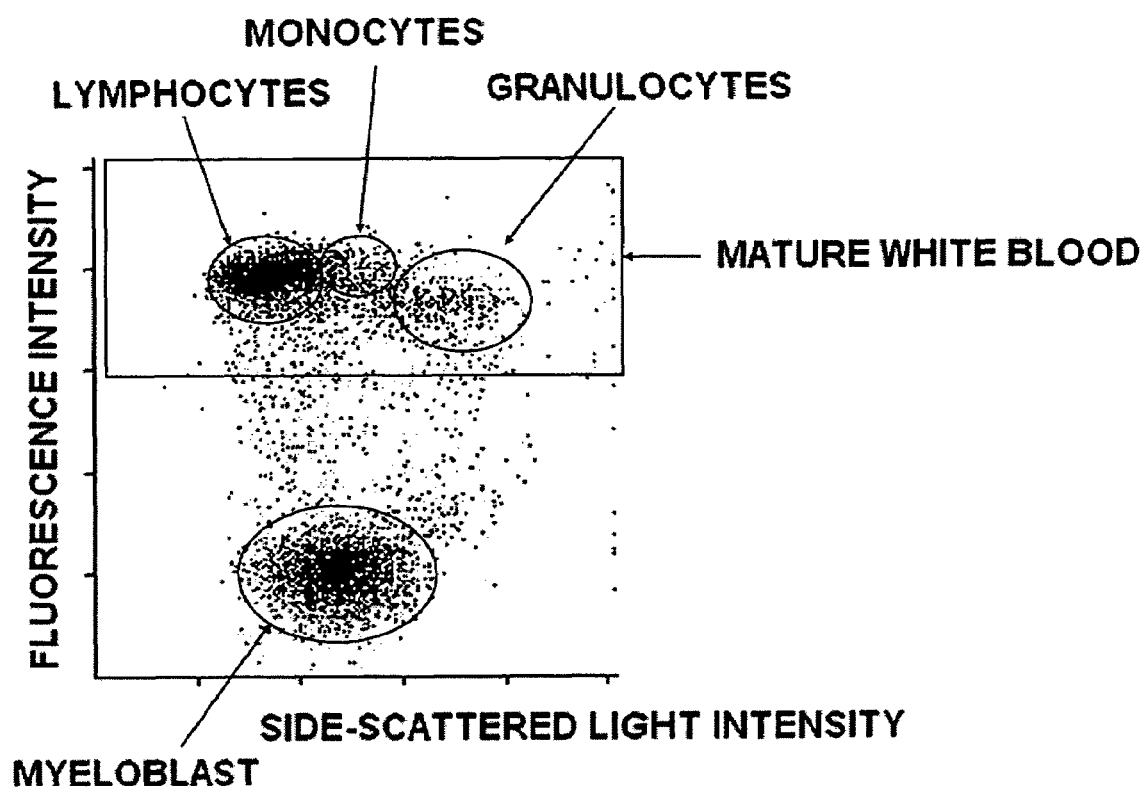
FIG. 12 is a second two-dimensional distribution chart in example 7.

Myeloblast ratio was calculated similarly as Example 1 except that the first reagent F was used in lieu of the first reagent A and the blood sample D was used in lieu of blood sample A. Myeloblast ratio was 45%. The first two-dimensional distribution chart drawn in Example 7 is shown in FIG. 11 and the second two-dimensional distribution chart is shown in FIG. 12. Mature leukocyte region where mature leukocyte appears was also set to the second two-dimensional distribution chart shown in FIG. 12.

Further, myeloblast ratio of the blood sample D calculated using a microscope was 58.5%. From the fact that myeloblast ratio measured in Example 7 and myeloblast ratio calculated using the microscope showed approximation, it has been confirmed that when a reagent of Example 7 is used, mature leukocyte and myeloblast in the blood sample can be identified accurately and myeloblast can be counted accurately.

Example 8

Myeloblast ratio was calculated similarly as Example 5 except that a blood sample G was used in lieu of the blood sample D. Myeloblast ratio was 5.5%. The first two-dimensional distribution chart drawn in Example 8 is shown in FIG. 13 and second two-dimensional distribution chart is shown in FIG. 14.

Further, myeloblast ratio of the blood sample E calculated using the microscope was 6.3%. From the fact that myeloblast ratio measured in Example 8 and myeloblast ratio calculated using the microscope showed approximation, it has been confirmed that when a reagent of Example 8 is used, mature leukocyte and myeloblast in the blood sample can be identified accurately and myeloblast can be counted accurately.

Figure 13:
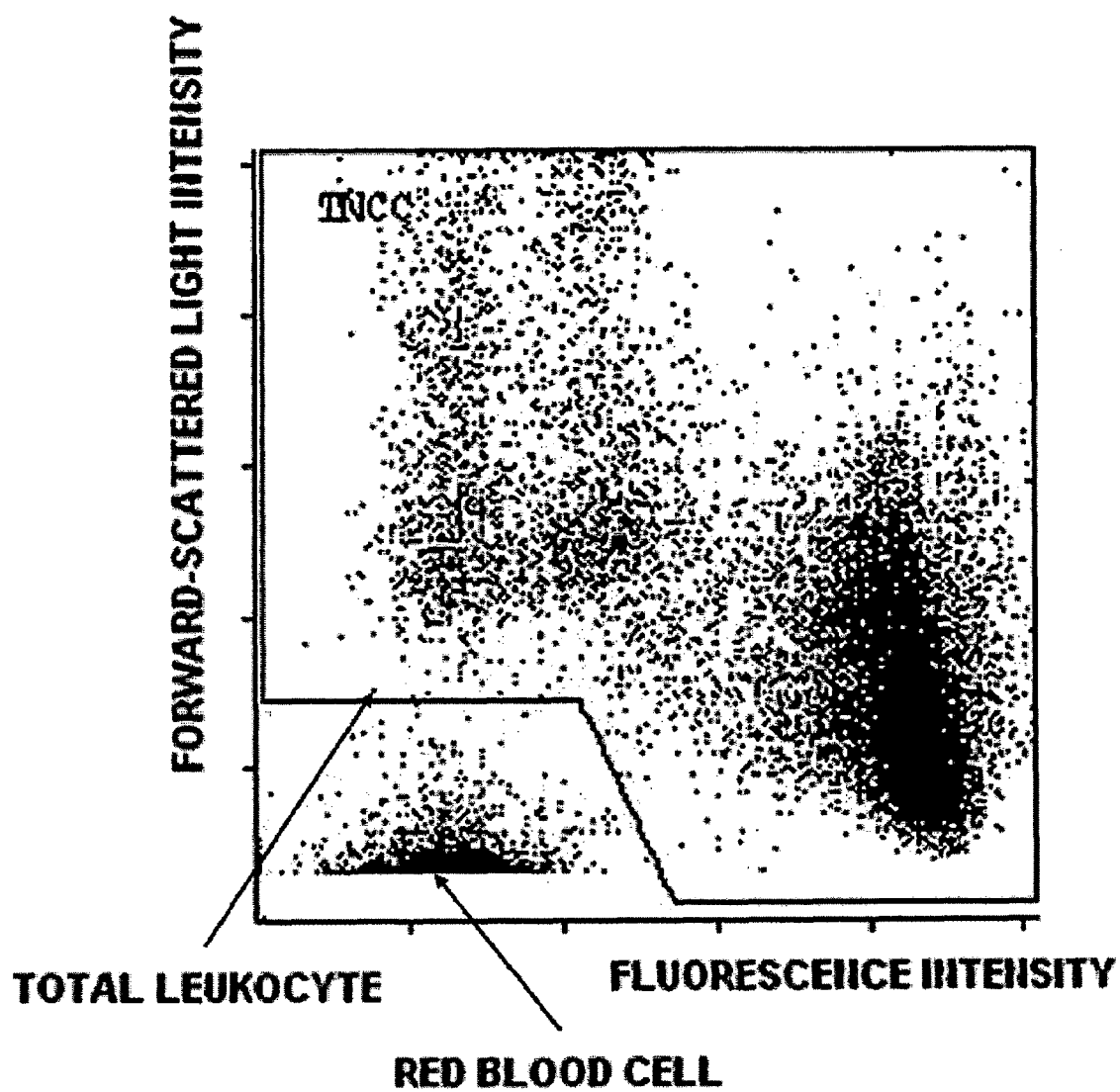
FIG. 13 is a first two-dimensional distribution chart in example 8.
Figure 14:
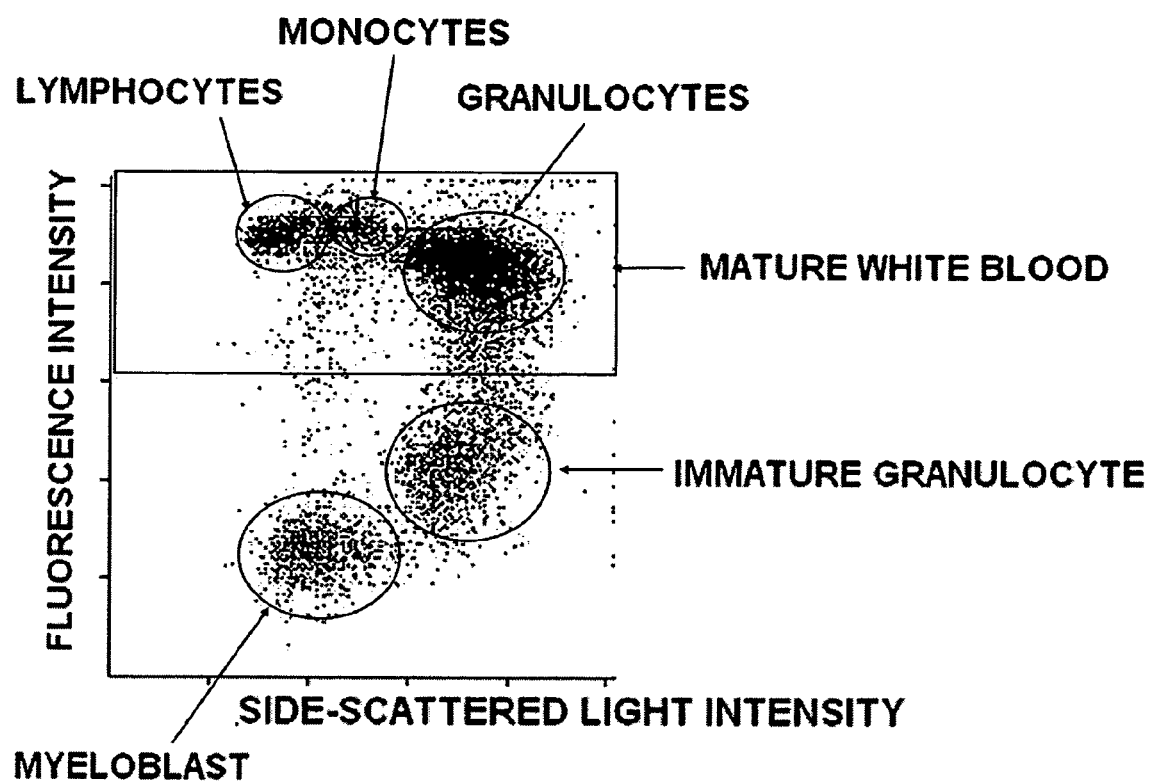
FIG. 14 is a second two-dimensional distribution chart in example 8.

Further, immature granulocyte region where immature granulocyte appears was set to the first two-dimensional distribution chart shown in FIG. 13, and the number of cells appearing in this region was counted as the number of immature granulocyte. Based on this value, ratio of immature granulocyte to total leukocyte count (immature granulocyte ratio) was calculated. Immature granulocyte ratio was 10%.

Further, immature granulocyte ratio of the blood sample E calculated using the microscope was 13%. From the fact that immature granulocyte ratio measured in Example 8 and immature granulocyte ratio calculated using the microscope showed approximation, it has been confirmed that when the reagent of Example 8 is used, mature leukocyte, myeloblast and immature granulocyte in the blood sample can be identified accurately and immature granulocyte as well as myeloblast can also be counted accurately.

Example 9

Figure 15:
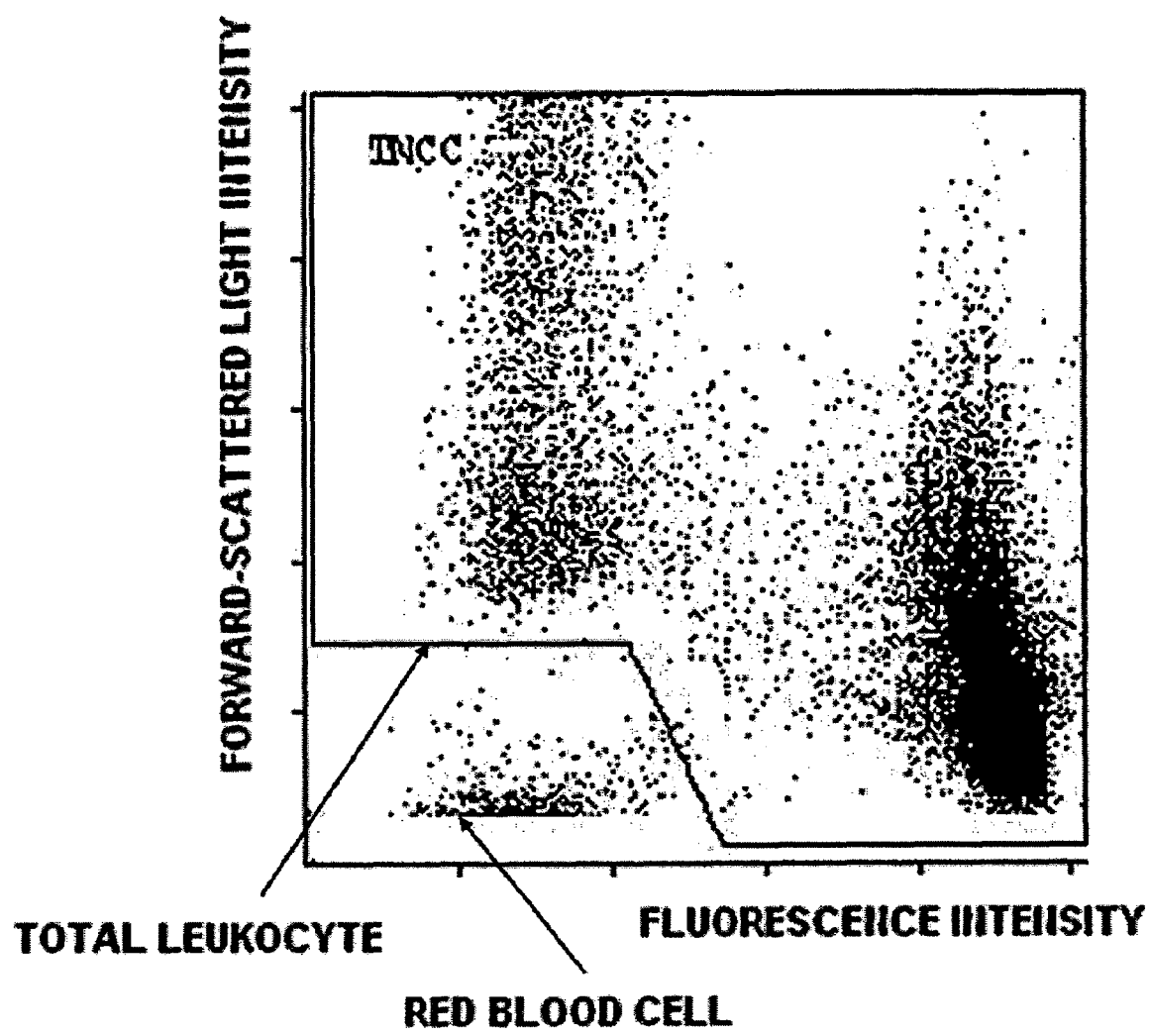
FIG. 15 is a first two-dimensional distribution chart in example 9.
Figure 16:
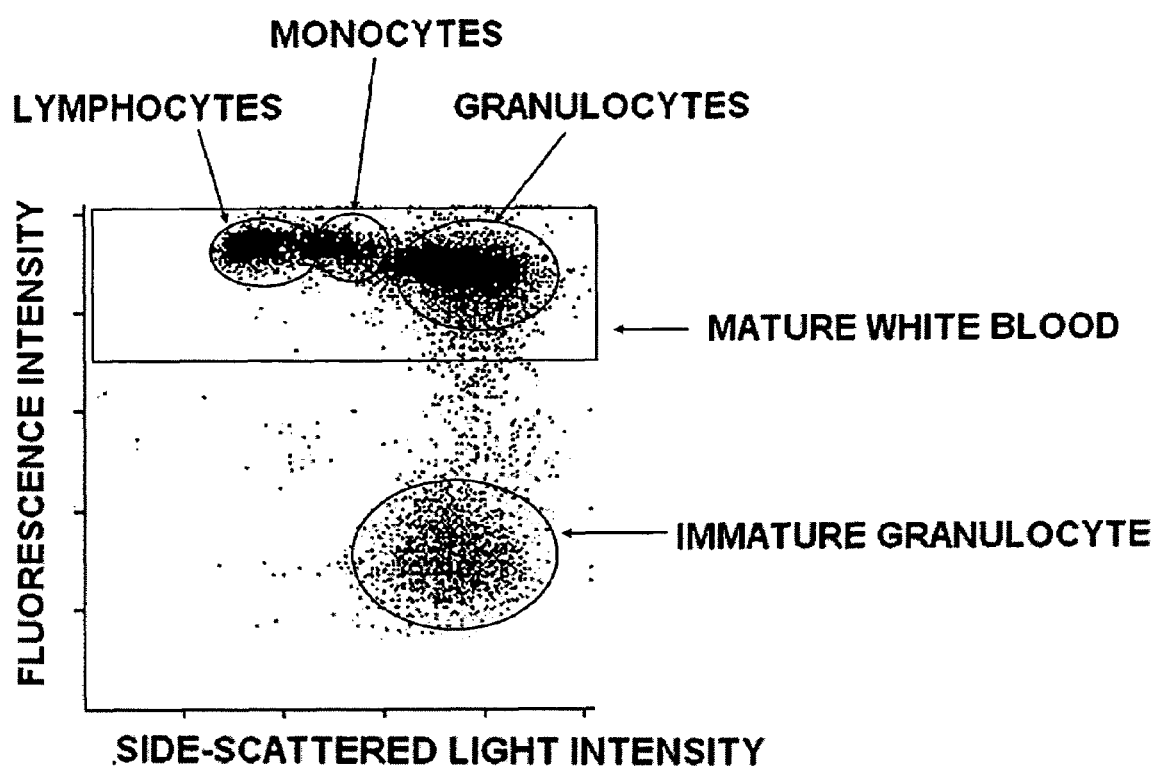
FIG. 16 is a second two-dimensional distribution chart in example 9.

Immature granulocyte ratio was calculated similarly as Example 5 except that the blood sample F was used in lieu of blood sample D. Immature granulocyte ratio was 12.4%. Meanwhile, the first two-dimensional distribution chart drawn in Example 9 is shown in FIG. 15 and second two-dimensional distribution chart is shown in FIG. 16.

Further, myeloblast ratio and immature granulocyte ratio of the blood sample E were calculated using the microscope, while immature granulocyte ratio was 10.8%. From the fact that immature granulocyte ratio measured in Example 9 and immature granulocyte ratio calculated using the microscope showed approximation, it has been confirmed that when the reagent of Example 9 is used, mature leukocyte and immature granulocyte in the blood sample can be identified accurately and immature granulocyte can be counted accurately.

The foregoing detailed description and examples have been provided by way of explanation and illustration, and are not intended to limit the scope of the appended claims. Many variations in the presently preferred embodiments will be obvious to one of ordinary skill in the art, and remain within the scope of the appended claims and their equivalents.

What is claimed is

1. A reagent for analyzing immature leukocyte contained in a sample, which reagent comprises a surfactant for giving damage to cell membrane of red blood cell and mature leukocyte, a solubilizing agent for causing contraction to damaged blood cell, a sugar, and a dye for staining nucleic acid,
wherein the reagent has electric conductivity from 0.1 to 2 mS/cm.

2. The reagent according to claim 1, wherein said surfactant is a polyoxyethylene-type nonionic surfactant represented by the following chemical formula;

in the formula, $R_1$ denotes alkyl group, alkenyl group or alkynyl group having from 10 to 25 carbon numbers, $R_2$ denotes —O— or

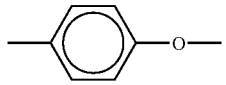

or —COO—, where n is from 10 to 40.

3. The reagent according to claim 1 wherein said solubilizing agent is at least one selected from the group consisting of sarcosine derivative, salt of sarcosine derivative, cholic acid derivative, and methylglucamide.

4. The reagent according to claims 1, wherein said sugar is at least one selected from the group consisting of xylitol, arabinose, glucose, mannitol, sorbitol, and ribitol.

5. The reagent according to claim 1 containing from 10 to 75 g/L of said sugar.

6. The reagent according to claim 1, which does not substantially contain sodium chloride.

7. The reagent according to claim 1, pH of which is from 5.0 to 9.0.

8. The reagent according to claim 1, osmotic pressure of which is from 150 to 600 mOsm/kg.

9. A reagent kit for analyzing immature leukocyte contained in a sample comprising a first reagent which comprises a surfactant for giving damage to cell membrane of red blood cell and mature leukocyte, a solubilizing agent for causing contraction to damaged blood cell, and an osmotic pressure regulator, and a second reagent containing a dye for staining nucleic acid.
wherein the first reagent has electric conductivity from 0.1 to 2 mS/cm.

10. The reagent kit according to claim 9, wherein said osmotic pressure regulator is at least one selected from the group consisting of sugar and amino acid.

11. The reagent kit according to claim 10, wherein said amino acid is at least one selected from the group consisting of glycine and alanine.

12. The reagent kit according to claim 10 containing from 1 to 50 g/L of said amino acid.

13. A reagent kit for analyzing immature leukocyte contained in a sample comprising a first reagent which comprises a surfactant for giving damage to cell membrane of red blood cell and mature leukocyte, a solubilizing agent for causing contraction to damaged blood cell, and a sugar, and a second reagent containing a dye for staining nucleic acid,
wherein the first reagent has electric conductivity from 0.1 to 2 mS/cm.

14. The reagent kit according to claim 13, wherein said surfactant is a polyoxyethylene-type nonionic surfactant represented by the following chemical formula;

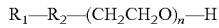

in the formula, $R_1$ denotes alkyl group, alkenyl group or alkynyl group having from 10 to 25 carbon numbers, $R_2$ denotes —O— or

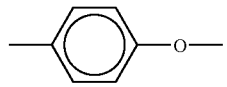

or —COO—, where n is from 10 to 40.

15. The reagent kit according to claim 13 wherein said solubilizing agent is at least one selected from the group consisting of sarcosine derivative, salt of sarcosine derivative, cholic acid derivative, and methylglucamide.

16. The reagent kit according to claim 13, wherein said sugar is at least one selected from the group consisting of xylitol, arabinose, glucose, mannitol, sorbitol, and ribitol.

17. The reagent kit according to claim 13 containing from 10 to 75 g/L of said sugar.

18. The reagent kit according to claim 13, which does not substantially contain sodium chloride.

* * * * *